United States Patent
Pianowski et al.

(10) Patent No.: US 10,105,339 B2
(45) Date of Patent: *Oct. 23, 2018

(54) INGENOL DERIVATIVES IN THE REACTIVATION OF LATENT HIV

(71) Applicant: AMAZÔNIA FITOMEDICAMENTOS LTDA., Fortaleza (BR)

(72) Inventors: Luiz Francisco Pianowski, Bragança Paulista (BR); Amilcar Tanuri, Rio de Janeiro (BR)

(73) Assignee: AMAZÔNIA FITOMEDICAMENTOS LTDA, Fortaleza-CE (BR)

( * ) Notice: Subject to any disclaimer, the term of this patent is extended or adjusted under 35 U.S.C. 154(b) by 895 days.

This patent is subject to a terminal disclaimer.

(21) Appl. No.: 14/382,060

(22) PCT Filed: Mar. 1, 2013

(86) PCT No.: PCT/BR2013/000063
§ 371 (c)(1),
(2) Date: Aug. 29, 2014

(87) PCT Pub. No.: WO2013/126980
PCT Pub. Date: Sep. 6, 2013

(65) Prior Publication Data
US 2015/0030638 A1  Jan. 29, 2015

(30) Foreign Application Priority Data

Mar. 2, 2012 (BR) .................... 10 2012 004739 0
Mar. 23, 2012 (BR) .................... 10 2012 006549 5

(51) Int. Cl.
| | |
|---|---|
| A61K 31/232 | (2006.01) |
| A61K 31/216 | (2006.01) |
| A61K 31/22 | (2006.01) |
| A61K 31/23 | (2006.01) |
| A61K 39/39 | (2006.01) |
| A61K 45/06 | (2006.01) |

(52) U.S. Cl.
CPC .......... *A61K 31/232* (2013.01); *A61K 31/216* (2013.01); *A61K 31/22* (2013.01); *A61K 31/23* (2013.01); *A61K 39/39* (2013.01); *A61K 45/06* (2013.01)

(58) Field of Classification Search
None
See application file for complete search history.

(56) References Cited

U.S. PATENT DOCUMENTS

2010/0204318 A1  8/2010  Ogbourne et al.

FOREIGN PATENT DOCUMENTS

| JP | H7165600 | 6/1995 | |
|---|---|---|---|
| WO | WO 2011/086424 | 7/2011 | |
| WO | WO-2011086423 A1 * | 7/2011 | ........... A61K 31/232 |

OTHER PUBLICATIONS

Opferkuch et al., On the Active Principles of the Spurge family (Euphogiaceae), 1982, 103:255-268.*
International Search Report for PCT/BR2013/000063 dated Apr. 25, 2013.
Warrilow D, Gardner J, Darnell GA, et al. HIV type I. inhibition by Protein Kinase C Modulatory Compounds. Aids Res Hum Retrov 2006,22(9):854-864.
Fujiwara M, Ijichi K, Tokuhisa K, et al. Mechanism of selective Inhibition of Human Immunodeficiency Virus by Ingenol Triacetate. Antimicrobial Agents and Chemotherp 1996,40(I):271-273.
Blanco-Molina M, Tron GC, Macho A, et al. Ingenol esters induce apoptosis in Jurkat cells through na AP-1 and NF-kB independente pathway. Chem & Biol 2001,8:767-778.

* cited by examiner

*Primary Examiner* — Kortney L. Klinkel
*Assistant Examiner* — Tori Strong
(74) *Attorney, Agent, or Firm* — B. Aaron Schulman, Esq.; Stites & Harbison, PLLC

(57) ABSTRACT

The present invention broadly relates to the use of certain ingenol derivatives as HIV reactivators of latent HIV virus in viral reservoirs. In another aspect, the present invention relates to an association comprising such ingenol derivatives and antiretroviral agents substantially active against actively replicating virus.

13 Claims, 8 Drawing Sheets

INGENOL DERIVATIVES IN THE REACTIVATION OF LATENT HIV

The present invention generally relates to certain ingenol derivatives and their use as reactivators of latent HIV virus in viral reservoirs. In another aspect, the present invention relates to associations and compositions comprising said ingenol derivatives and anti-retroviral agents substantially active against actively replicating virus.

BACKGROUND OF THE INVENTION

It is known that the human immunodeficiency virus (HIV) is the etiological agent responsible for AIDS—acquired immune deficiency syndrome, a fatal disease that is characterized by the destruction of the immune system, disabling the organism to react appropriately to life threatening opportunistic infections.

Highly active anti-retroviral therapy (known as HAART) has been used to suppress HIV replication. It consists of the treatment commonly known as anti-AIDS "cocktail", with at least three active anti-retroviral compounds, containing reverse transcriptase inhibitors, integrase, protease and entry.

However, in infected patients, the virus from reservoirs of CD4+T lymphocyte cells latently infected (i.e. containing residual latent proviral DNA, integrated into the genome of host cells) quickly resumes the viral replication after cessation of the HAART treatment.

Thus, HIV remains a chronic viral infection when such persistent latent infection is not fought.

According to the current rationale in the art, the activation of latent viruses contained in such reservoirs, in the presence of anti-retroviral drugs, intends to make them detectable by the body immune system and accessible to active medication against the virus to cause destruction of cells expressing viral proteins, by reaction of the host immune system and/or such that the cells are brought to apoptosis, inhibiting the replication of viruses that come out from the reservoirs by action of the anti-retroviral drugs, thus exhausting the reservoir of HIV persistent infection and enabling the total eradication of the infection.

In other words, the selective induction of latent infection allows anti-retroviral drugs and the antiviral immune response to access and eradicate residual HIV infection—i.e. not just temporarily stabilizing the immune system without later use of anti-retrovirals, but definitely suppressing the HIV infection in the human body.

Glossary

In the context of the present invention, the term "latent virus" or "latent HIV virus" means the DNA sequence of the virus that causes the acquired immune deficiency syndrome that is imported into the nucleus of infected cells and integrated into the host cell genomic DNA which, after such integration, can become latent, i.e., with undetectable levels of viral gene expression, thus not allowing the detection of virus and infected cells by the host immune system and causing infection persistence, including those patients under highly active anti-retroviral therapy (HAART) with undetectable viral load for long periods.

The expression "viruses under active replication" relates to the active viral DNA in the infected cell, with the expression of viral genes into the host cell and production of viral particle progeny.

The expression "viral reservoirs" relates to the host cells where the HIV virus may persist undetected by the immune system in its latent form, even during highly active anti-retroviral therapy (known as HAART). Such reservoirs are distributed along the host organism, including the brain, bone marrow, lymphoid tissue and genitourinary tract. The main viral latent reservoir of HIV virus is in CD4+ memory T cells.

The expression "reactivation of latent HIV virus" means the reactivation of the virus with the expression of viral latent genes and the subsequent formation of new viral particles, making the infected cell again detectable by the host immune system.

The expression "active anti-retroviral agents" relates to agents, active principles or medicines that act on different stages of the HIV life cycle, but do not act substantially, or act only in a limited way, against HIV virus in a latent infection present in host viral reservoirs.

The term "viral load", also known as "viral titer", means an estimate of the number of viral particles present in a fluid sample from a patient according to the result of detection methods used.

The term "adjuvant" relates to an agent or active principle to be delivered in addition to the initial, primary or main treatment of a disease, disorder or illness. The isolated effect of the "adjuvant" does not effectively address the disease or disorder, but complements the treatment and improves the survival rates, quality of life or curing rates that would be usually obtained with the primary or main therapy.

The term "liposome" means small vesicles consisting of one or more concentric phospholipids bilayers which spontaneously arrange themselves in an aqueous medium. They can be used as medicine controlled release systems. Liposomes can protect the active principle from chemical, physical and enzymatic degradation, enable the increase of drug concentration in the target site, can be used as not-toxic excipients to solubilize hydrophobic drugs and may extend the lifetime of vesicle and drug in the circulation, generating positive effects on the characteristics of pharmacokinetics and toxicity of the active principle.

The term "nanoparticles" means ultra-thin particles with 1 to 100 nanometers in diameter that can encapsulate or protect active principles or drugs and present potentially advantageous properties when used as a controlled drug release system. The nanoparticles may protect the active principle from chemical, physical and enzymatic degradation, enable an increase of drug concentration in the target site, can be used as not-toxic excipients to solubilize hydrophobic drugs and may extend the lifespan of the drug in circulation, producing positive effects on pharmacokinetics and toxicity of the active principle.

The expression "active principle" means a biologically active substance in a pharmaceutical composition which may contain one or more active principles in its formulation.

The term "association" means any form of proper dosage, in combination, mixture, formulation, preparation or equivalent, to be administered to a person, containing at least a ingenol derivative of formula I (component a) and at least one anti-retroviral agent substantially active against actively replicating virus (component b).

The term "pharmaceutically acceptable excipients" relates to inert substances used in pharmaceutical compositions as diluents or vehicles. Examples of pharmaceutically acceptable excipients are described in publications "Remington: The Science and Practice of Pharmacy", 20$^{th}$ edition or later, Lippincott Publishing House, Williams & Wilkins; "Pharmaceutical Dosage Forms and Drug Delivery Systems (1999) H. C. Ansel et al., 7th edition, Lippincott Publishing House, Williams & Wilkins; "Handbook of Pharmaceutical Excipients" (2000) A. H. Kibbe et al, 3rd edition, American Pharmaceutical Association Publishing House.

The term "apoptosis" means the process of cell death not followed by autolysis which, as a process of programmed cell death, occurs in an organized manner, differently from necrosis.

The expression "downregulation of CD4 receptor" or "downregulation of CD4 HIV receptor" means the disappearance of CD4 receptor from the surface of plasma membrane of CD4+ cells, which makes the cell refractory to subsequent infections by AIDS virus or other viruses that use the CD4 receptor, creating a state of cell immunity to superinfection.

The expression "anti-retroviral treatment" means highly active anti-retroviral therapy (known as anti-AIDS cocktail or HAART) usually comprising at least three active anti-retroviral medications among reverse transcriptase inhibitors, which can comprise nucleosides, inhibiting viral replication by interruption of the nucleotide chain synthesized by the enzyme, or non-nucleosides that inhibit viral replication by binding in the active site of the reverse transcriptase enzyme, integrase inhibitors, which inhibit the integration of viral DNA into the host cell genomic DNA, entry or fusion inhibitors, which interfere with the binding and entry of virus into the host cell and protease inhibitors, which inhibit the formation and release of new viral particles from the cell membrane of the host cell.

DESCRIPTION OF THE INVENTION

It is understood in the text below that mention to "anti-retroviral agents active against viruses under active replication" relates to agents that do not substantially act, or act only in a limited way, on HIV viral reservoirs in the human body.

The present invention relates, in a first aspect, to the use of one or more ingenol derivatives of formula I below:

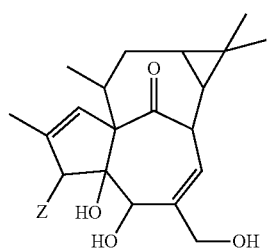

Formula I used in the preparation of product adjuvant in the treatment of HIV infection or AIDS treatment, wherein Z is Z1

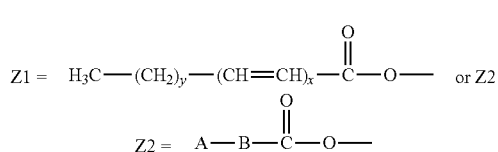

such that, when Z=Z1, ingenol derivatives of the invention are as depicted in the formula II below:

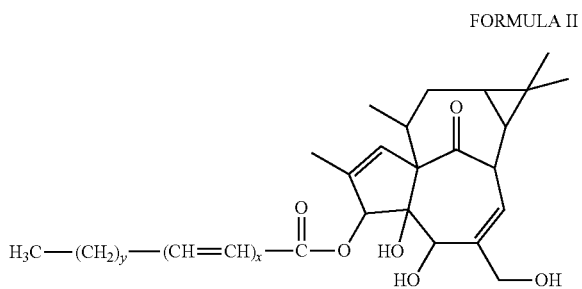

FORMULA II x and y are integers, x varies between 2 and 10 and y varies between 2 and 7.

Particularly for formula II, x varies between 3 and 5 and y varies between 3 and 4. Particular embodiments of formula II can be cited, wherein x=3 and y=4:

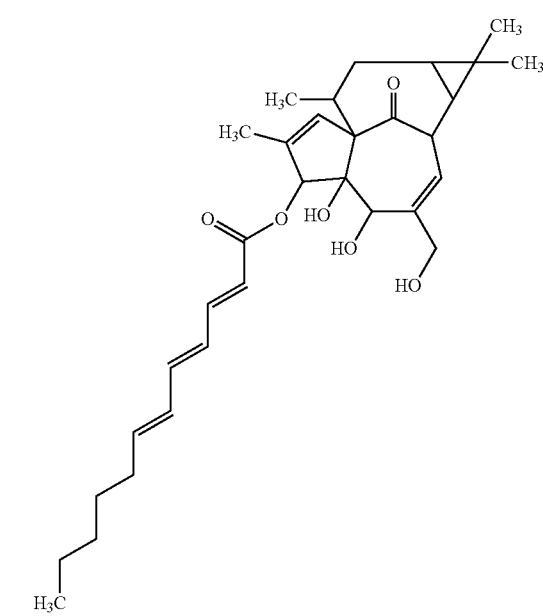

(3-(2,4,6-dodecatrienoyl)-ingenol)

and wherein x = 4 and y = 4:

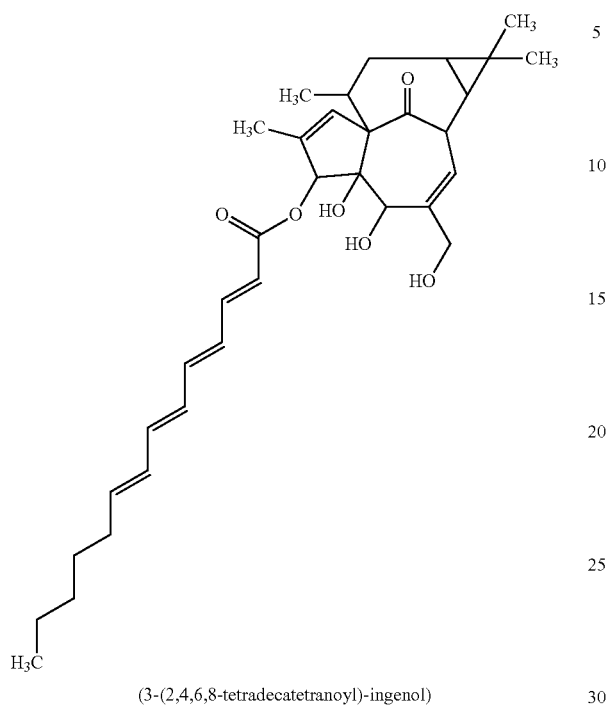

(3-(2,4,6,8-tetradecatetranoyl)-ingenol)

In relation to formula I, when Z=Z2, ingenol derivatives of the invention are as depicted in the formula III below:

FORMULA III

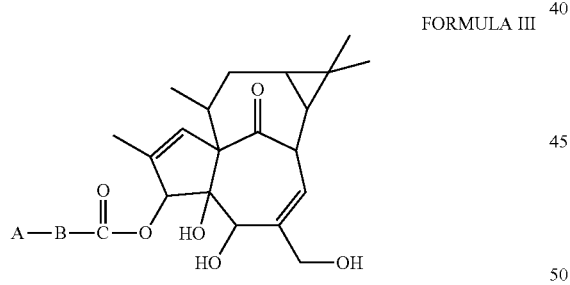

wherein A is phenyl, $CH_3$— or $CH_2$=CH—, and
B is —CH=CH—, [—$CH_2$—]$_q$ or [—$CH_2$—]$_w$,
wherein q is an integer ranging between 1 and 10, preferably between 2 and 6, and w is an integer ranging between 1 and 10, preferably between 8 and 10, provided that:
when A is phenyl, B is —CH=CH—;
when A is $CH_3$—, B is [—$CH_2$—]$_q$;
when A is $CH_2$=CH—, B is [—$CH_2$—]$_w$ Particular examples of ingenol derivatives of formula III suitable for the invention, in a non-exclusive manner, are structures A, B, C and D below:

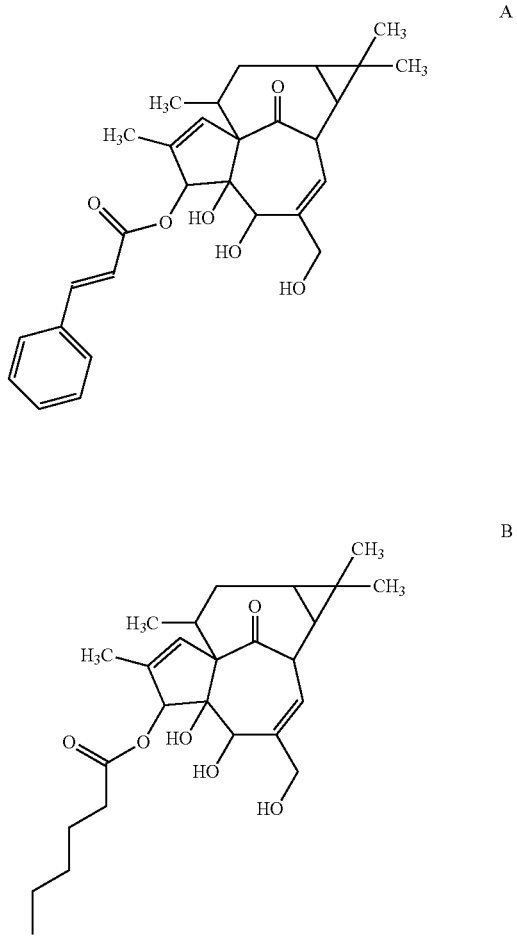

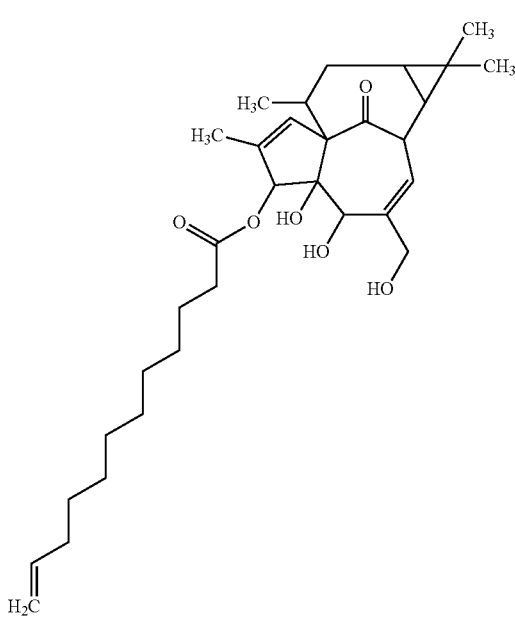

Products derived from the invention, particularly when Z=Z2, with 3-cinnamyl (Example A), 3-hexanoyl (Example B), 3-dodecanoyl (Example C) and 3-dodeca-11-enoyl (Example D) radicals, were selected according to their low potential of generating toxic degradation products after metabolism.

Particularly, Formula I of Ingenol Derivatives of the Invention Presents the Following Conformation:

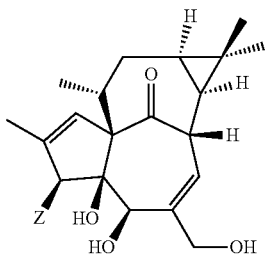

Ingenol derivatives of the invention can be prepared by different ways known to a person skilled in the art, by synthetic or semi-synthetic processes, for example, from plant raw materials (such as the active fraction resulting from the chromatographic separation of a butanolic extract from *Euphorbia tirucalli* L. latex, described in the international patent application WO2007000618), or from any other appropriate raw materials, for example, free base ingenol, terpenes, etc.

In another aspect, the invention relates to the use of ingenol derivatives of formula I above, on reactivation of the latent HIV virus in viral reservoirs of the human body. It is an use in medical therapy.

In another aspect, the invention relates to a useful association for the treatment or prevention of infection of the HIV virus, comprising one or more ingenol derivatives of formula I, and at least one active anti-retroviral agent in viruses under active replication, particularly selected among nucleoside or non-nucleoside reverse transcriptase inhibitors, protease inhibitors, co-receptor antagonists, retroviral integrase inhibitors, viral adsorption inhibitors, specific viral transcription inhibitors, cyclin-dependent kinase inhibitors and combinations thereof.

Still according to the meaning employed herein, it is understood that associations of one or more ingenol derivatives of formula I (component a) and one or more antiretroviral agents (component b) may be available in a single dosage unit (e.g., tablet, capsule, ampoule, bag, etc.) or in different dosage units, in which the components (a) and (b) are provided for administration to a patient together or separately, either simultaneously or sequentially.

There is no particular limitation on the dosage form for the association of the invention, including, besides those already mentioned, liposomes and nanoparticles or any other forms known by a person skilled in the art.

Particularly, the invention relates to pharmaceutical compositions containing the association cited before, and pharmaceutically acceptable excipients.

In another particular aspect, the composition of the invention can further contain other active principle(s) different from the ingenol(s) of formula I and antiretroviral agents. Particularly, the composition of the invention comprises one or more compounds capable of reactivating the latent HIV virus in viral reservoirs in the human body, other than those ingenol derivatives of formula I.

In another aspect, the invention relates to an adjunct useful to reactivate latent HIV virus in viral reservoirs in the human body, characterized in that it comprises one or more ingenol derivatives of formula I, and pharmaceutically acceptable excipients.

In another aspect, the invention relates to a method of treatment or prevention of HIV infections, characterized in that it comprises administering an association to a patient in need of such treatment, as mentioned above. Said treatment comprises administering the association components at the same time or sequentially.

In yet another particular aspect, the invention relates to a method for reactivating latent HIV virus in viral reservoirs in the human body, characterized by administering one or more ingenol derivatives of formula I to a patient.

Among the reverse transcriptase nucleoside inhibitors suitable for the invention, there can be cited, in a non-exclusive manner, the compounds AZT (zidovudine), 3TC (lamivudine), d4T (stavudine), abacavir, ddI (didanosine), ddC (zalcitabine), FTC (emtricitabine), PMPA (R)-9-(2-phosphonylmethoxypropyl)adenine), tenofovir, adefovir, amdoxovir, elvucitabine, alovudine, racivir, apricitibine, phosphazide and fozivudine tidoxil.

Among the non-nucleoside reverse transcriptase inhibitors of the invention, there can be cited, in a non-exclusive manner, the compounds nevirapine, efavirenz, delavirdine, loviride, etravirine, (+)calanolide, rilpivirine and lersivirine.

Among the protease inhibitors suitable for the invention, there can be cited, in a non-exclusive manner, the compounds ritonavir, lopinavir, nelfinavir, saquinavir, indinavir, atazanavir, amprenavir, darunavir, fosamprenavir and tipranavir.

Among the integrase inhibitors suitable for the invention, there can be cited, in a non-exclusive manner, the compounds raltegravir, elvitegravir and dolutegravir.

Among the fusion Inhibitors suitable for the invention, there can be cited, in a non-exclusive manner, the compounds enfuvirtide and tifuvirtide.

Among the co-receptor inhibitors suitable for the invention, there can be cited, in a non-exclusive manner, the CCR5 co-receptor inhibitors vicriviroc and maraviroc.

The ingenol derivatives of the invention, the active antiretrovirals actively on replicating virus or the association of the invention containing them can be administered to a patient by any appropriate path, for example, by oral, parenteral, intravenous, intra-arterial, Intraperitoneal, transdermal, sublingual, rectal, intramuscular, transbucal, intranasal, liposomal, inhalation, vaginal, subcutaneous, intra-adipose, intraocular, intra-articular or intrathecal, as well as administration using a catheter or stent, etc.

There is no specific restriction regarding the dosage forms used with ingenol derivatives of the invention or with the inventive association. For example, tablets, pill, capsules, granules, pellets and the like can be used for oral administration. For liquid oral administration solutions, dispersions, suspensions, emulsions, oils, etc., can be used.

The dosage form may be of immediate, slow or controlled release.

EXAMPLES

Exemplary embodiments of the invention are given below, in a non-limited sense to such examples, since limitations of the invention are set forth only in the attached claims.

Z1 Derivatives of Ingenol of the Invention

Examples 1 and 2 relate to a 1:1 mixture of two ingenol derivatives of formula (I), when Z=Z1, which are 3-(2,4,6-dodecatrienoyl)-ingenol (x=3 and y=4) and 3-(2, 4,6,8-tetradecatetranoyl)-ingenol (x=4 and y=4), a mixture herein called KyoII, in dimethyl sulfoxide solution at a concentration of 20 mM. Such a solution is used to make dilutions in culture media to achieve the active concentration.

KyoII mixture can be obtained, for example, as mentioned in the patent application WO2007000618, by chromatographic separation of a latex butanolic extract from *Euphorbia tirucalli* plant.

Example 1

The test below was performed with cell line called J-lat, derived from Jurkat lineages, which works as an in vitro model of latent HIV-1. Similarly to resting CD4+ T cells infected with HIV-1 virus, J-Lat cells carry a complete genome of HIV-1 integrated into the cell genome regions that can be activated; however, the transcription of these regions is temporarily inhibited. Additionally, the latent provirus integrated in J-Lat cell lines encodes a GFP (green fluorescent protein) gene, thus providing a fluorescent reporter of HIV-1 transcriptional activity. These cells were treated with TNF-α (20 ng/ml) for viral re-activation as a positive control and the effect was compared with the mixture of ingenol Z1 derivatives. The expression of HIV viral genes was monitored by the GFP reporter gene during 48-72 hours after treatment with TNF-α through flow cytometry.

Jlat clone cells 6.3 and 8.4 (provided by Dr. B. Matija Peterlin, University of California, San Francisco, Calif., USA) were maintained in RPMI culture medium (Rosewell Park Memorial Institute—sold by Invitrogen, USA) containing 10% FBS (fetal bovine serum). The Jlat clone cells 6.3 and 8.4, in a concentration of $10^6$ cells/mL, were induced with different concentrations of the derived KyoII for 24 hours and TNF-α was used as a positive control at 20 ng/mL concentration.

After the induction step, the cells were washed with RPMI medium and then re-suspended in RPMI medium containing 10% fetal bovine serum and cultivated for more than 24 hours to obtain the induction of latent virus.

After induction, 30,000 cells were read in a BD-Excalibur flow cytometer (Beckton Dickinson Company and Co., USA) for reading cells expressing the GFP marker protein. A cell sample was not induced and remained 48 hours in culture to serve as a simulated control (referred to as "mock"), thus marking the spontaneous induction of the provirus (background).

Figure 1A:
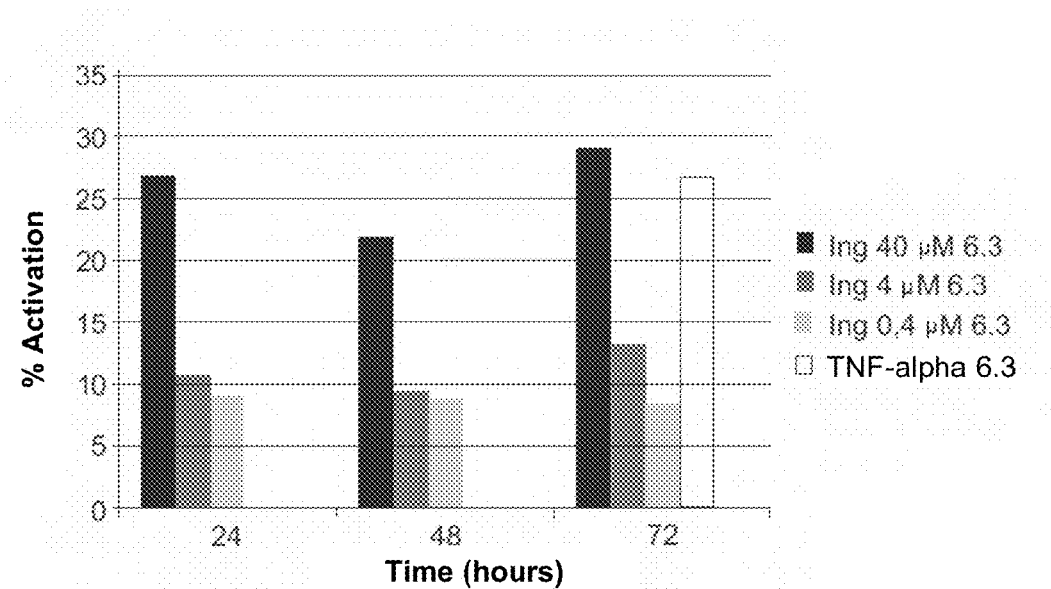
FIG. 1A represents a graph of latency induction in Jlat 8.4 clone with different concentrations of an ingenol derivative of the invention, hereinafter KyoII, when Z=Z1 in the Markush structure shown above. 20 ng of TNF-α were used as positive control and the results are shown as % of induced cells.
Figure 1B:
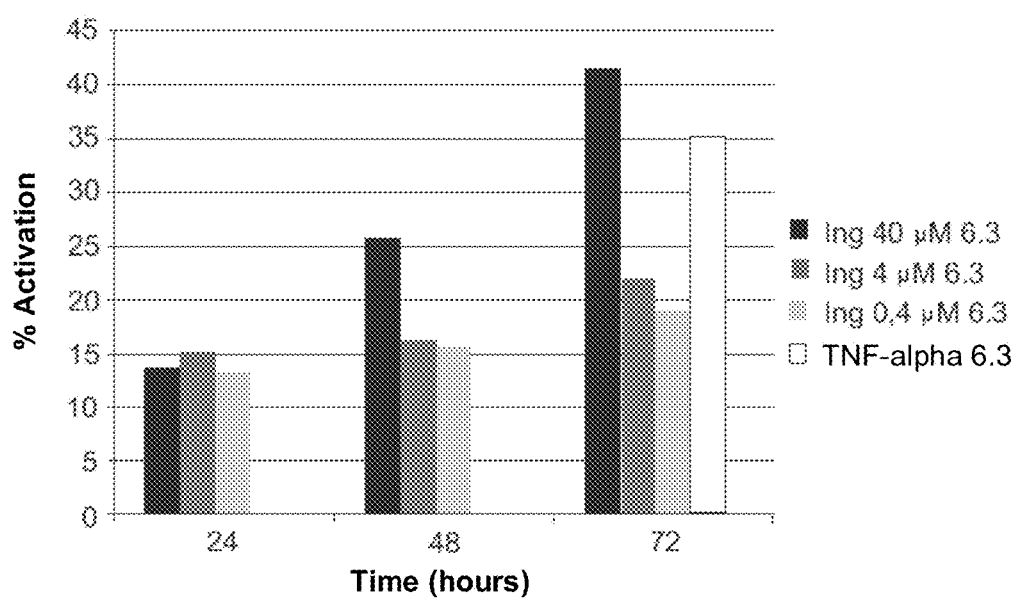
FIG. 1B represents a graph of latency induction in Jlat 6.3 clone with different concentrations of the KyoII derivative mentioned above. 20 ng of TNF-α were used as positive control and the results are shown as % of induced cells.

The histogram of FIGS. 1A and 1B shows that the KyoII sample, after a 24-hour induction, was able to activate the latent virus present in Jlat clones 6.3 and 8.4 in a dose-dependent manner, and even at very low doses (0.4 μm) it was able to induce up to 8% of Jlat clone cells 6.3 and 8.4 in culture, and at 40 μm concentration it induced almost 30% of the cells, thus overcoming the TNF-α potency.

Figure 1C:
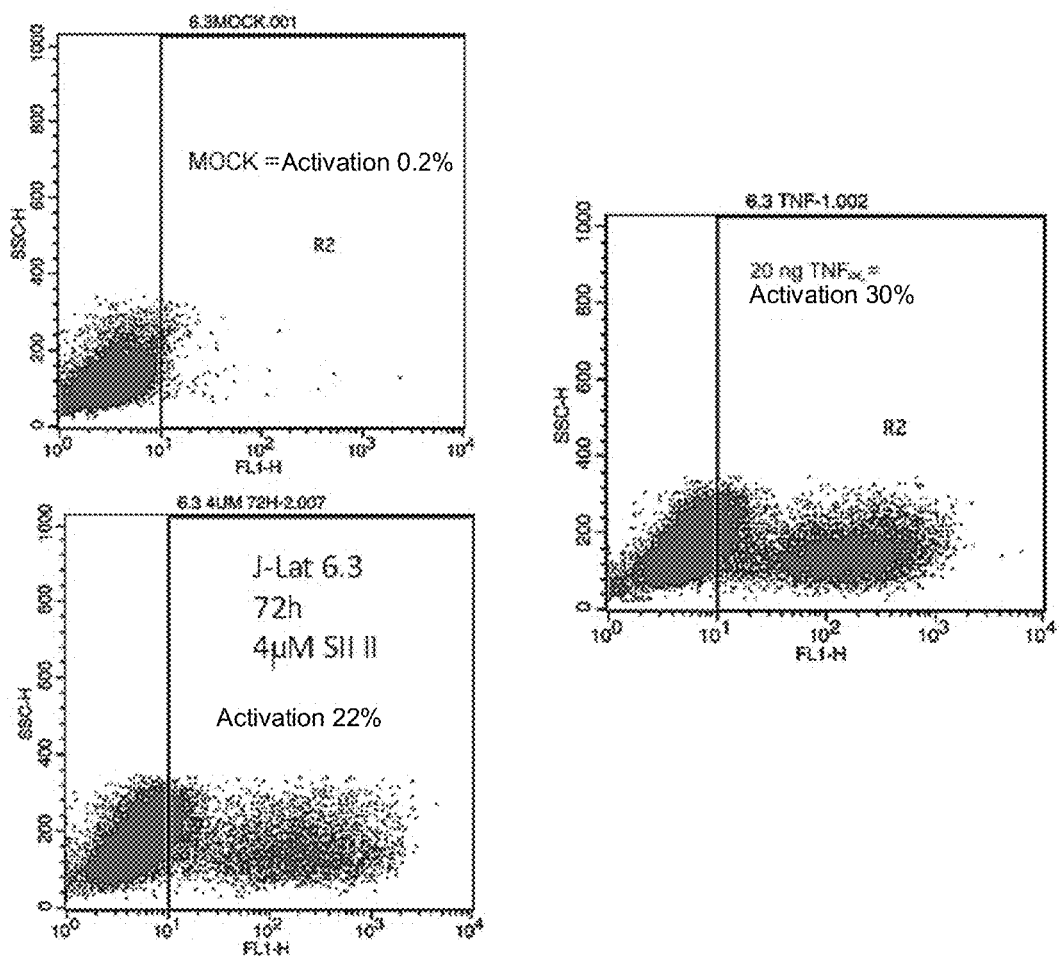
FIG. 1C is a histogram showing the latency induction in Jlat 6.3 clone with 4 μm of the KyoII derivative mentioned above. In this case, 20 ng of TNF-α were used as positive control and the results are also shown as % of induced cells.

FIG. 1c shows histograms presenting raw data obtained from the Cellquest software (Becton Dickinson and Company, USA) showing the latency induction in a Jlat 6.3 clone, following the same protocol cited above with 4 μm KyoII. In this case, 20 ng of TNF-α were used as positive control and the results are also shown as % of induced cells.

Example 2—Toxicity

Figure 2:
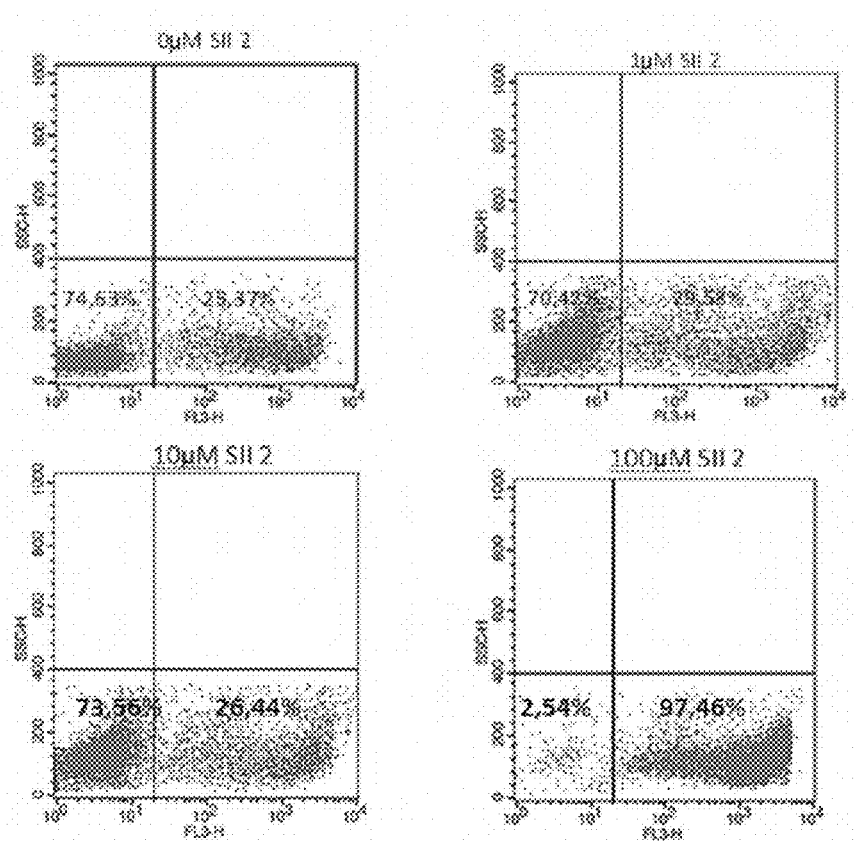
FIG. 2 is a histogram showing the apoptosis activation in human PBMC (peripheral blood mononuclear cells) cells cultivated for 72 h with the different concentrations of the ingenol derivative KyoII mentioned above. The drug concentration is shown beside each graphic and the % of cells under apoptosis is marked on the left quadrant of each graph.
Figure 3:
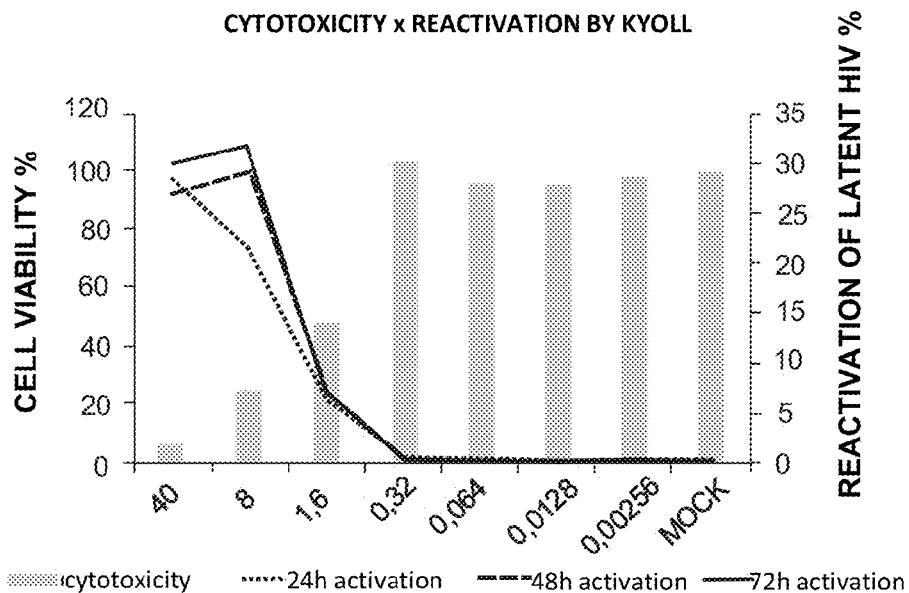
FIGS. 3 to 6 are composite graphs which show the induction of HIV latency in Jlat 6.3 clone and the corresponding cytotoxicity, for both the KyoII derivative (where Z=Z1) and the A, B and C derivatives (where Z=Z2).
Figure 4:
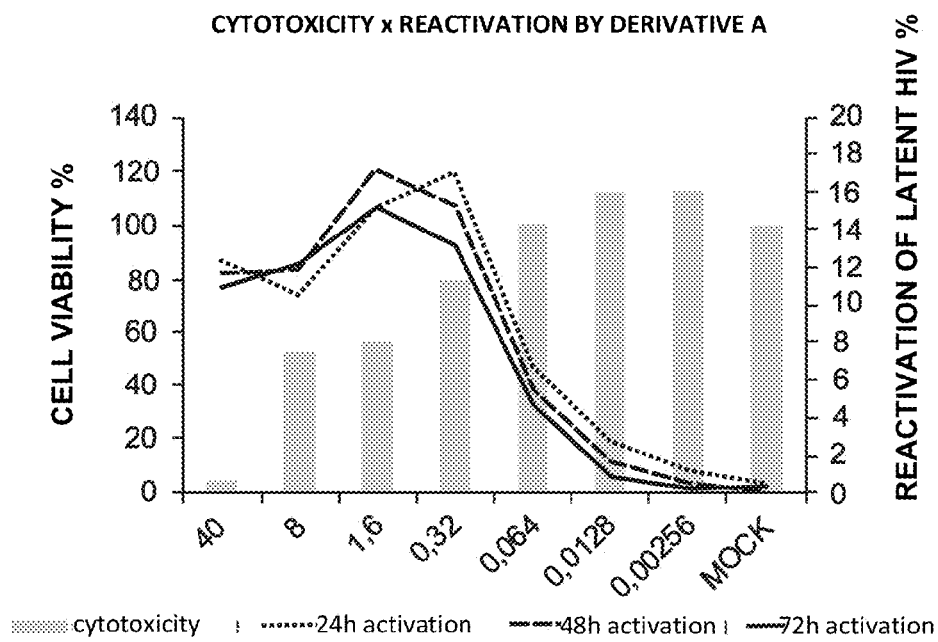
Figure 5:
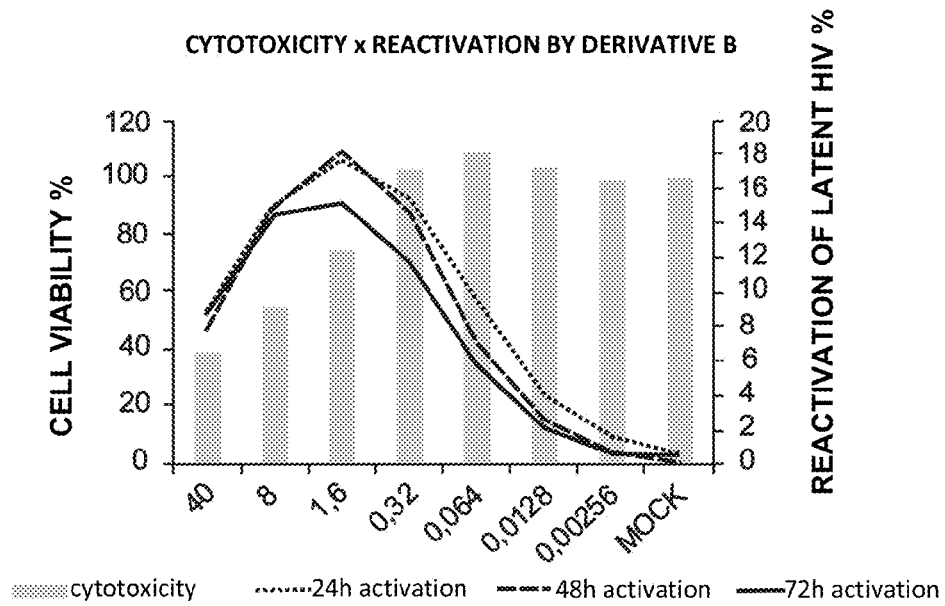
Figure 6:
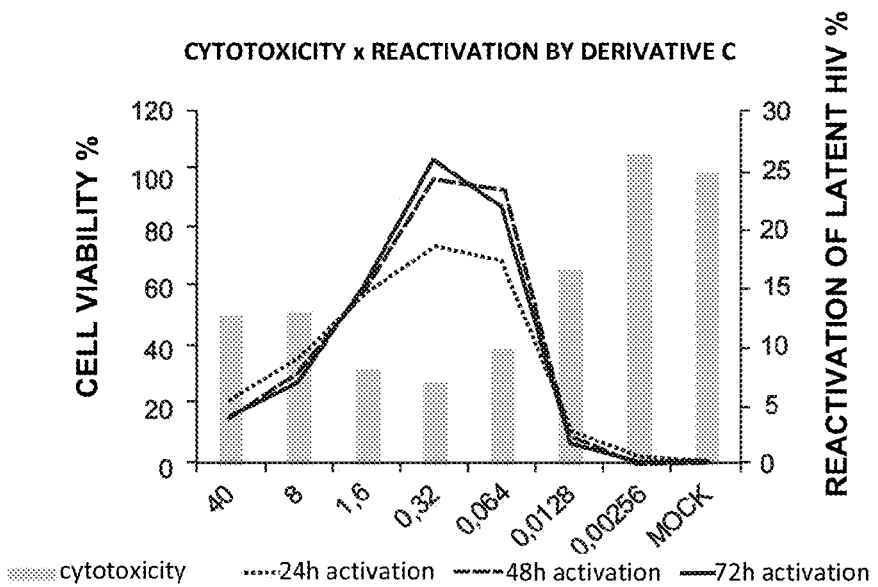

It is verified in this test that the derivatives in the KyoII mixture of example 1, at concentrations that induce latency in J-lat cells, are not cytotoxic to human PBMC cells. Thus, human PBMC cells at a concentration of $10^6$ cells/mL were cultured in RPMI medium with 10% fetal bovine serum, exposed to different concentrations of KyoII and left in culture for 72 hours. After exposure, the cells were stained with propidium iodide. Thus, the cells were centrifuged at 1000 G for 3 minutes and washed with the same volume with 1×PBS (without $Ca^{2+}$ and $Mg^{2+}$, Cat No. 9240, Irvine Scientific Company, USA) containing 2% fetal bovine serum. PBS, or "Phosphate Buffered Saline" is saline buffered with phosphate. This wash was repeated 3 times and the cells were suspended in 1×PBS containing 500 µg of propidium iodide and allowed to incubate for 5 min at 4° C. until being read by flow cytometry. After incubation, 30,000 cells were read in a BD-Excalibur flow cytometer. With this protocol it was possible to see the amount of cells with degraded DNA or in advanced stages of apoptosis (FIG. 2). It was possible to observe that, for concentrations up to 10 µM, the ingenol derivative is not cytotoxic to PBMCs cells and there was 100% of death at 100 µM.

Example 3—Cytotoxicity Verification vs. Reactivation

This example aimed at correlating the cytotoxicity effects and HIV reactivation both for the KyoII mixture of ingenol derivatives, wherein Z=Z1 of examples 1 and 2 above, and for 3 ingenol derivatives of formula I, wherein Z=Z2, indicated above as A, B and C. In these cases, a concentration of $10^6$ cells/mL JLat 6.3 was induced with different concentrations of KyoII, A, B, and C for 24 hours. After the induction step, the cells were washed with RPMI medium and re-suspended in RPMI medium containing 10% fetal bovine serum and cultivated for another 24 hours for the induction of latent virus.

After induction, 30,000 cells were read in a BD-Excalibur flow cytometer for reading cells expressing the GFP marker protein. A cell sample was not induced and remained 48 hours in culture to serve as a simulated control (referred to as "mock"), thus marking the spontaneous induction of the provirus (background). The staining technique with propidium iodide was used for measuring the cytotoxicity of compounds. Thus, the cells were centrifuged at 1000 G for 3 minutes and washed with the same volume with 1×PBS (without $Ca^{2+}$ and $Mg^{2+}$, Cat No. 9240, Irvine Scientific Company, USA) containing 2% fetal bovine serum. This washing was repeated 3 times and the cells were suspended in 1×PBS containing 500 µg propidium iodide and incubated for 5 min at 4° C. until being read by flow cytometry. After incubation, 30,000 cells were read in a BD-Excalibur flow cytometer (Beckton Dickinson and Co., USA). With this protocol it was possible to precisely the amount of cells with degraded DNA or in advanced stages of apoptosis by measuring with precision cell viability (FIG. 2). The results were plotted in a composed graph, which compared the induction ability of compounds versus their cytotoxic activity.

Example 4—Test with HIV+ Human Cells Originated from Patients Under Anti-Retroviral Treatment It was tested, in this experiment, the ability of ingenol derivative, of formula I, wherein Z=Z2, mentioned as B, of activating latent cells from patients who were already under anti-retroviral treatment for more than 1 year with undetectable viral load. A patient (identified as MLV) was selected, which had already been under treatment with zidovudine+ lamivudine (AZT+3TC) and efavirenz for over 14 months, with undetectable viral load and CD4>500 cells/mm$^3$. 20 mL of blood was collected from the patient in a EDTA (ethylene diamine tetra acetic acid) tube and PBMC cells were isolated, which were placed in RPMI culture medium with 10% fetal bovine serum and 50 IU/mL of IL2 (interleukin 2), and grown in 2 bottles with 5 mL of identical cells (106/mL) with different selective compositions. 10 µM efavirenz (antiviral) was added to the control bottle to block viral replication that would eventually arise from cultured cells. In another test bottle both efavirenz (10 µM) and the B derivative of the invention (1 µM) were included. Both bottles were cultured at 37° C. for 72 hours and then the intracellular RNA from the PBMCs was extracted with a RNEasy kit (QiaGen Company, USA) and the amount of HIV-1 genomic RNA was dosed by semi-nested real time PCR reaction using primers that hybridize with the gag region of the HIV-1 genome taking the non-spliced viral RNA GAG1 Sense I, II ((5' TCAGCCCAGAAGTAATAC-CCATGT 3'; genome position 1280-1303; TM=58.3° C.) and SK431 antisense I (5' TGCTATGTCAGTTCCCCTTG-GTTCTCT 3'; genome position 1474-1500; TM=61.5° C.) as 10 rounds of PCR and followed by a semi-nested real time reaction with primers GAG1 Sense I, II (5' TCAGCCCA-GAAGTAATACCCATGT3'; genome position 1280-1303; TM=58.3° C.) and antisense AG2 II (5' CACTGTGTTTAG-CATGGTGTTT 3'; genome position 1341-1362 55.1 TM=57° C.) and identified with GAG3 probe (FAM-AT-TATCAGAAGGAGCCACCCCACAAGA-TAMRA; genome position 1311-1337; TM=61° C.). The semi-nested PCR real-time reaction for detecting HIV-1 vRNA was carried out as follows: the extracted cell RNA was diluted 10 times in water and treated with Dnase I (Invitrogen Corporation, USA) for 15 minutes to remove any trace of proviral DNA. Then, DNase I was inactivated under incubation at 70° C. for 10 min in the presence of 1 mM EDTA and 50 mM DTT (dithiothreitol). Reverse transcription of RNA was conducted with random hexamer primers and SuperScript III (brand enzyme for cDNA synthesis, from Invitrogen, USA) at 42° C. for 60 min. cDNA was then subjected to PCR reactions. The pair of primers used in the 1$^{st}$ PCR round was GAG1 and SK431 that amplifies the gag inner region of HIV-1. This first round was run on a conventional PCR machine in a 25 µL volume with 5 µL of cDNA, 20 mM tris(hydroxymethyl)aminomethane (pH 8.3), 50 mM KCl, 2 mM $MgCl_2$, 0.4 mM DNTPs (deoxynucleotide triphosphates) and 1 U Ampli-Taq (DNA polymerase, from Applied Biosystems, USA), and 50 ng of each primer. The PCR conditions were: 94° C. for 3 min, followed by 15 cycles at 94° C. for 30 s, 55° C. for 30 s and 72° C. for 1 min. The product of this first PCR underwent a 2$^{nd}$ semi-nested real-time PCR, in a ABI Prism 7000 machine real-time PCR (from Applied Biosystems, USA) using a TaqMan reaction mixture in a total volume of 25 µl, with 2 µl of the 1$^{st}$ round diluted 50 times with 0.2 µm of primers GAG1 and GAG2, and 0.2 µm FAM GAG3 probe. The real-time PCR conditions were: 50° C. for 2 min and 95° C. for 10 min, followed by 50 cycles of 95° C. for 15 seconds and 60° C. for 1 min. The sizes of amplicons were 221 bp for the 1$^{st}$ round and 83 bp for (real-time) PCR.

Figure 7:
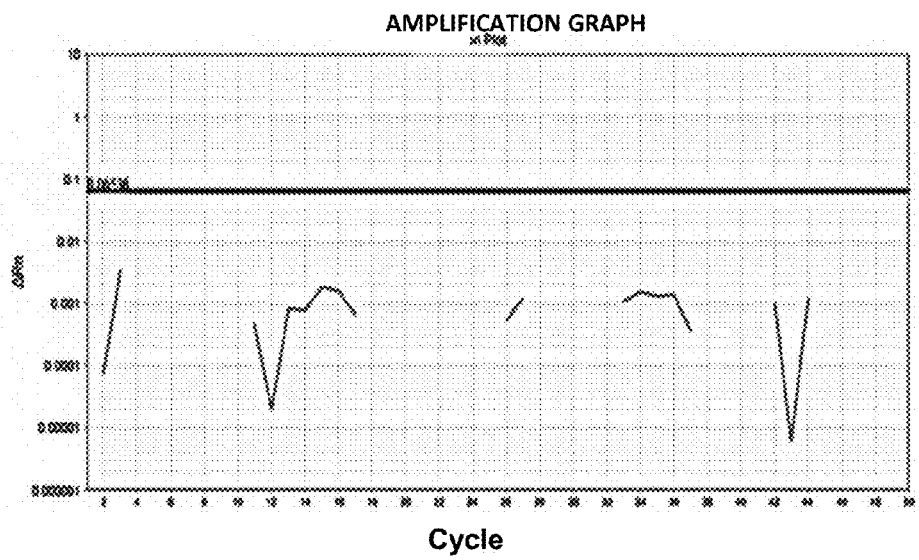
FIGS. 7 and 8 are PCR (polymerase chain reaction) graphs for blood cells from patients treated exclusively with efavirenz (FIG. 7), and with a mixture of efavirenz and the ingenol B derivative of the invention (FIG. 8).

It can be observed in FIG. 7 that the PBMC cultures from MLV patient containing 10 µM efavirenz did not produce intracellular vRNA and, therefore, did not generate detectable product in real time semi-nested PCR.

Figure 8:
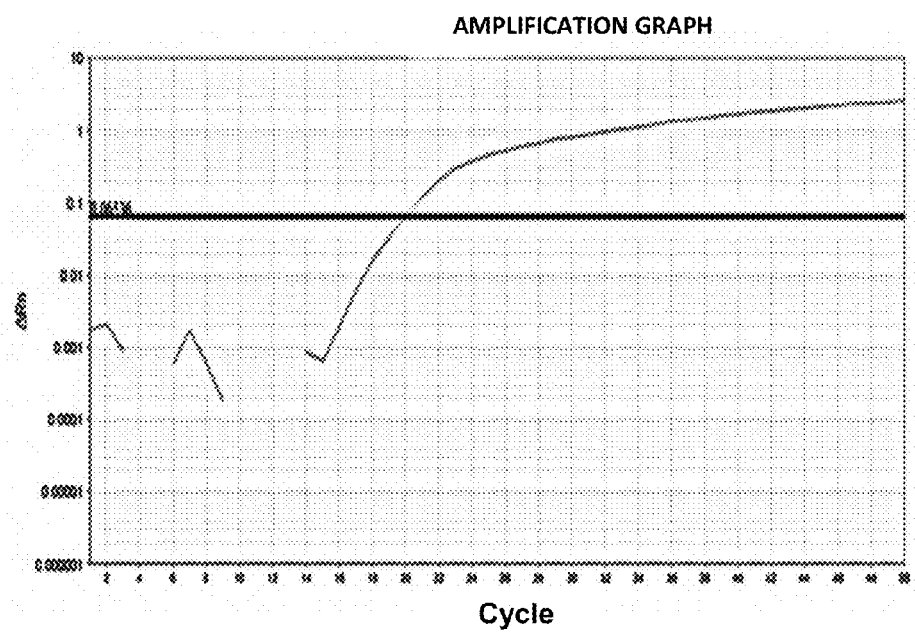

On the other hand, in PBMC culture in which 10 µm efavirenz and 1 µM B derivative B of the invention were added—FIG. 8—the emergence of intracellular HIV-1 vRNA, a sign of HIV latent virus in these blood cells, is verified.

Example 5

Downregulation of CD4 receptor on the surface of human CD4+T lymphocytes and macrophages and pig-tail monkeys (*Macaca nemestrina*).

It is verified in this test that ingenol derivatives of formula 1, when Z=Z2, at concentrations that activate HIV from latency in Jlat cells in example 3, downregulate the expression of CD4 cell receptor on the surface of HIV-human and SIV-pig-tail monkey CD4+T lymphocytes and macrophages. For this experiment PBMC cells from human and monkeys were isolated from peripheral blood with isolation through Ficoll-Hypaque density gradient (mixture of high density hydrophilic neutral polysaccharides that readily dissolves in aqueous solution. "Ficoll" is a trademark of GE Healthcare Bio-Sciences, USA). Thus, PBMC cells from human and monkeys, at concentration of $10^6$ cells/mL, were cultured in RPMI medium with 10% fetal bovine serum for 24 hours and adhered cells (monocytes differentiating into macrophages) were separated from the cell supernatant which contained total lymphocytes. Those two distinct populations of cells were exposed to different concentrations of A, B and C derivatives of the invention, and left in culture for 72 hours. After exposure, the cells were stained with specific lymphocyte monoclonals (anti-CD3) and monocytes/macrophages (anti-CD14) simultaneously with an anti-CD4. Thus, the cells were centrifuged at 1000 G for 3 minutes and washed with the same PBS volume (without $Ca^{2+}$ and $Mg^{2+}$, Cat. No. 9240, Irvine Scientific, USA) containing 2% fetal bovine serum. This wash was repeated 3 times and the cells were suspended in 1×PBS containing a 1/1000 dilution of relevant antibodies and left to incubate for 30 min at 4° C. until being read in flow cytometry. After incubation, 30,000 cells were read in a BD-Excalibur flow cytometer (from Beckton Dickinson and co., USA) and the populations were separated and the CD4 receptor density was estimated at different concentrations of the B derivative, assuming cell density without B derivative as 100%. Molecules already known to downregulate CD4 were also placed in these experiments, for comparison purposes with A, B and C derivatives, such as prostratin, bryostatin and PMA (phorbol 12-myristate-13-acetate, a phorbol diester).

Figure 9:
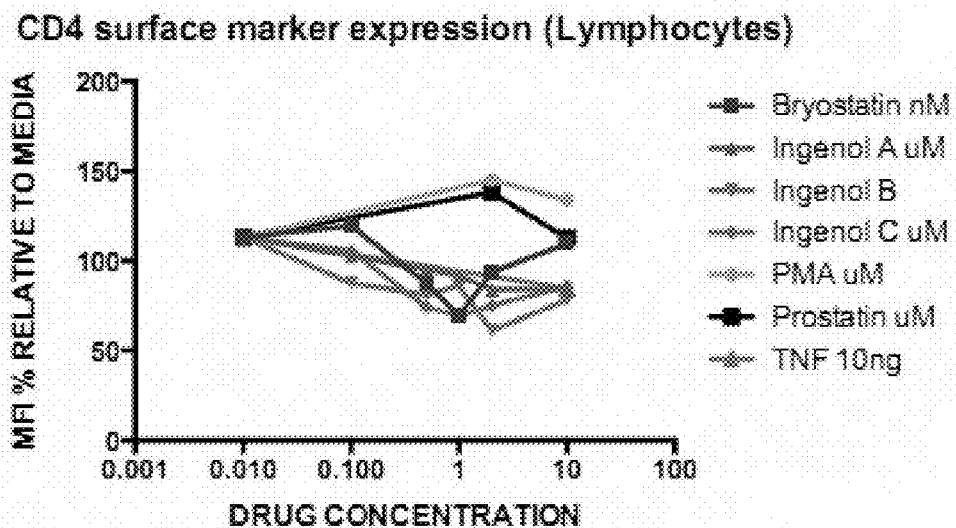
FIGS. 9 to 12 are flow cytometry readings, indicating down modulation of CD4 HIV-1 receptor on the surface of human and monkey lymphocytes, for the KyoII derivative (where Z=Z1) and for the A, B and C ingenol derivatives (where Z=Z2).
Figure 10:
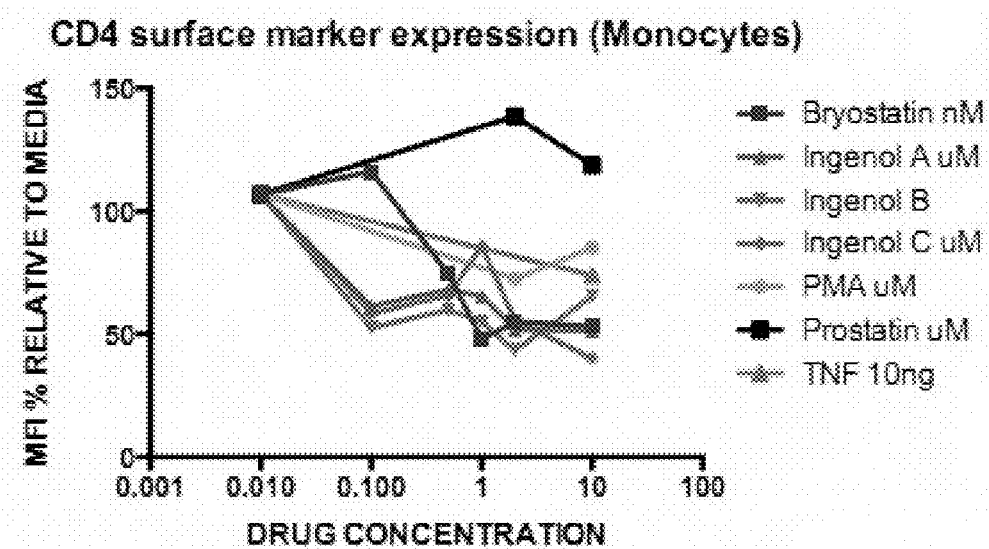
Figure 11:
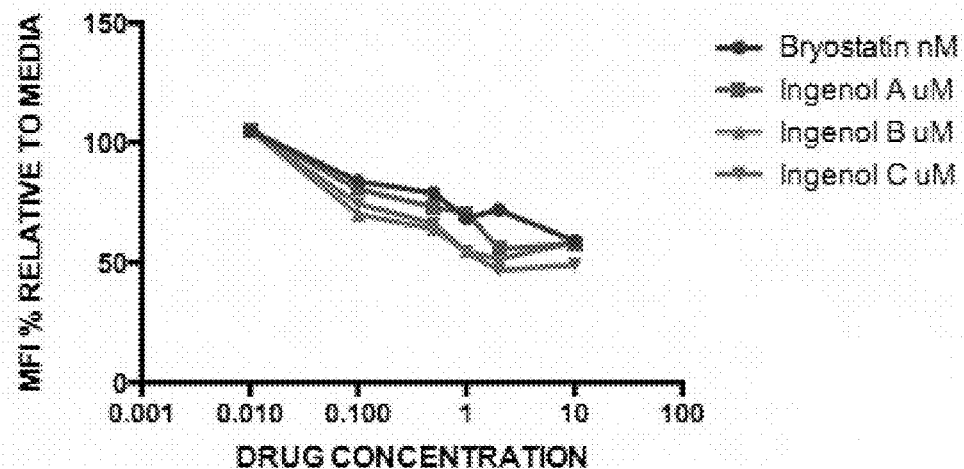
Figure 12:
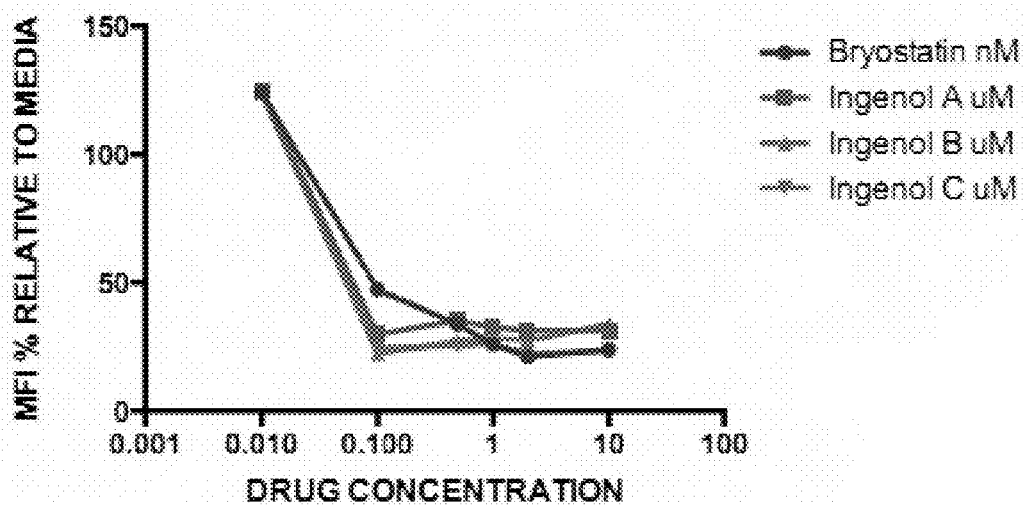

It is noted that ingenol Z2 derivatives of the invention were able to downregulate the expression of CD4 HIV-1 receptor on the surface of human (FIG. 11) and *Macaca nemestrina* lymphocytes (FIG. 9). Similarly, these compounds also down regulated CD4 on human (FIG. 12) and *Macaca nemestrina* (FIG. 10) monocytes/macrophages. It was remarkable the greater power of Z2 ingenol derivatives in the downregulation of CD4 of monkey cells when compared with comparative molecules (prostratin, bryostatin and PMA, see FIGS. 9 and 10).

The A, B and C ingenol derivatives were able to downregulate the main HIV receptor (CD4) on the surface of the infection targeted cells. Thus, it has been proven that the ingenol derivatives of the invention, besides of activating HIV from latency, hinder the ongoing of the virus infection by blocking its entry into new cells,

Example 6

Process of obtaining ingenol from an active fraction resulting from the chromatographic separation of butanolic extract from latex of *Euphorbia tirucalli* L. (hereinafter ingenol pool), described in the international patent application WO2007000618

A hydrolysis reaction was carried out with 18 g of ingenol pool eluted in 300 mL of methanol and 6 mL of sodium methoxide. The reaction was monitored by HPLC analysis every 30 minutes at 214 and 290 nm in YMC Pro C18, 4.6×50 mm, 3 µm column, with A-B gradient of 5-70% in 7 minutes, at 1.5 mL/min. Solvents: solvent A—0.1% TFA in water, solvent B—0.08% TFA in acetonitrile.

The reaction was neutralized with 1 ml of glacial acetic acid. The subsequent purification was conducted in 75% solution of ethyl acetate in heptane applied in a flash column containing 300 g of silica. The column was balanced with the same solvent. Ingenol was eluted in 100 g of ethyl acetate. Elution was monitored with a UV detector at 290 nm. The combined fractions were evaporated.

Example 7

Preparation of Ingenol-5,20-Acetonide Intermediate, to Protect Hydroxyl Groups 5 and 20

A reaction was conducted for ingenol acetonide formation in 7.34 g of hydrolyzed ingenol from example 6 (1.00 equiv; 21.1 mmol) eluted in 250 mL of acetone (34.1 volEquiv) with 76.0 mg of (1S)-(+)-10-camphor sulfonic acid (C2107; 0.0104 weightEquiv; 99%). The reaction was monitored by HPLC analysis every 15 minutes at 214 and 290 nm in YMC Pro C18, 4.6×50 mm, 3 µm column, with A-B gradient of 5-70% in 7 minutes, at 1.5 mL/min. Solvents: solvent A—0.1% TFA in water, solvent B—0.08% TFA in acetonitrile. After 1.5 h reaction, 78% 5,20-ingenol acetonide and 9.8% ingenol were detected. The reaction was neutralized with 140 µL of triethylamine (47.9 mEq; 1.01 mmol). Purification of 5,20-ingenol acetonide was conducted by evaporation at 35° C./30'/10 Torr, followed by crystallization from toluene.

Example 8

Esterification of 5,20 acetonide, followed by deprotection of the obtained intermediate, to prepare ingenol cinnamate (example A of the structure of formula III, for Z=Z2).

Esterification 3.60 g of 5,20-ingenol acetonide (1.00 equiv; 9.27 mmol), produced according to example 7, were eluted in 80 mL of acetonitrile (22.2 volEquiv) with 3.09 g of cinnamic anhydride (1.50 equiv; 13.9 mmol, and 4.53 g of cesium carbonate (1.50 equiv; 13.9 mmol).

The reaction was monitored by HPLC analysis every 15 minutes at 214 and 290 nm in YMC Pro C18, 4.6×50 mm, 3 µm column, with A-B gradient of 5-70% in 7 minutes, at 1.5 mL/min. Solvents: solvent A—0.1% TFA in water, solvent B—0.08% TFA in acetonitrile.

The obtained intermediate, 5,20-isopropylidene-ingenol-3-cinnamate, was then subjected to extraction and purification.

Extraction of the product of this step of the synthesis step in dichloromethane and water was performed. The organic phase was dried with magnesium sulfate and evaporated at 35° C./30'/10 Torr. This was followed by purification through solubilization in 5% ethyl acetate in heptane, and then applied in flash column containing 80 g of silica. The column was equilibrated with the same solvent. Thereafter, the column was washed with 5% ethyl acetate in heptane solution. The 5,20-isopropylidene-ingenol-3-cinnamate intermediate was eluted in 10% ethyl acetate in heptane solution. Elution was monitored by HPLC with UV detector at 290 nm. The combined fractions were evaporated at 35° C./30'/10 mbar.

Deprotection

For deprotection of the intermediate structure, 4.46 g of 5,20-isopropylidene-ingenol-3-cinnamate (1.00 equiv, 8.29 mmol; 96%) were eluted in 80 mL of methanol (19.9 volEquiv) plus 4.60 mL of 1N hydrochloric acid (1M; 0.555 equiv; 4.60 mmol). This was followed by extraction with toluene and water. The organic phase was dried with magnesium sulfate and evaporated at 35° C./30'/10 Torr.

Ingenol 3-cinnamate was obtained with purity of nearly 97%.

Example 9

Esterification of 5,20-acetonide, followed by deprotection of the obtained intermediate, to prepare ingenol 3-caproate (example B of formula III structure, for Z=Z2).
Esterification 3.60 g of 5,20-ingenol acetonide (1.00 equiv; 9.27 mmol), produced according to example 7, were eluted in 80 mL of acetonitrile (22.2 volEquiv) with 2.98 g of caproic anhydride (1.50 equiv; 13.9 mmol, and 4.53 g of cesium carbonate (1.50 equiv; 13.9 mmol).

The reaction was monitored by HPLC analysis every 15 minutes at 214 and 290 nm in YMC Pro C18, 4.6×50 mm, 3 μm column, with A-B gradient of 5-70% in 7 minutes, at 1.5 mL/min. Solvents: solvent A—0.1% TFA in water, solvent B—0.08% TFA in acetonitrile.

The obtained intermediate, 5,20-isopropylidene-ingenol-3-caproate, was then subjected to extraction and purification.

Extraction of the product of this step of the synthesis step in dichloromethane and water was performed. The organic phase was dried with magnesium sulfate and evaporated at 35° C./30'/10 Torr. This was followed by purification through solubilization in 5% ethyl acetate in heptane, and then applied in flash column containing 80 g of silica. The column was equilibrated with the same solvent. Thereafter, the column was washed with 5% ethyl acetate in heptane solution. The 5,20-isopropylidene-ingenol-3-caproate intermediate was eluted in 10% ethyl acetate in heptane solution. Elution was monitored by HPLC with UV detector at 290 nm. The combined fractions were evaporated at 35° C./30'/10 mbar.
Deprotection For deprotection of the intermediate structure, 4.20 g of 5,20-isopropylidene-ingenol-3-caproate (1.00 equiv, 8.29 mmol; 96%) were eluted in 80 mL of methanol (19.9 volEquiv) plus 4.60 mL of 1N hydrochloric acid (1M; 0.555 equiv; 4.60 mmol). This was followed by extraction with toluene and water. The organic phase was dried with magnesium sulfate and evaporated at 35° C./30'/10 Torr.

Ingenol 3-caproate was obtained with purity of nearly 97%.

Example 10

Esterification of 5,20-acetonide, followed by deprotection of the obtained intermediate, to prepare ingenol 3-dodecanoate (example C of formula III structure, for Z=Z2).
Esterification 3.60 g of 5,20-ingenol acetonide (1.00 equiv; 9.27 mmol) produced according to example 7, were eluted in 80 mL acetonitrile (22.2 volEquiv) with 4.17 g of dodecanoic acid (1.50 equiv; 13.9 mmol, and 4.53 g of cesium carbonate (1.50 equiv; 13.9 mmol).

The reaction was monitored by HPLC analysis every 15 minutes at 214 and 290 nm in YMC Pro C18, 4.6×50 mm, 3 μm column, with A-B gradient of 5-70% in 7 minutes, at 1.5 mL/min. Solvents: solvent A—0.1% TFA in water, solvent B—0.08% TFA in acetonitrile.

The obtained intermediate, 5,20-isopropylidene-ingenol-3-dodecanoate, was then subjected to extraction and purification.

Extraction of the product of this step of the synthesis step in dichloromethane and water was performed. The organic phase was dried with magnesium sulfate and evaporated at 35° C./30'/10 Torr. This was followed by purification through solubilization in 5% ethyl acetate in heptane, and then applied in flash column containing 80 g of silica. The column was equilibrated with the same solvent. Thereafter, the column was washed with 5% ethyl acetate in heptane solution. The intermediate 5,20-isopropylidene-ingenol-3-dodecanoate was eluted in 10% ethyl acetate in heptane solution. Elution was monitored by HPLC with UV detector at 290 nm. The combined fractions were evaporated at 35° C./30'/10 mbar.
Deprotection For deprotection of the intermediate structure, 4.90 g of 5,20-isopropylidene-ingenol-3-dodecanoate (1.00 equiv, 8.29 mmol; 96%) were eluted in 80 mL methanol (19.9 volEquiv) with 4.60 mL of 1N hydrochloric acid (1 M; 0.555 equiv; 4.60 mmol). This was followed by extraction with toluene and water. The organic phase was dried with magnesium sulfate and evaporated at 35° C./30'/10 Torr.

Ingenol 3-dodecanoate ingenol was obtained with purity of nearly 97%.

Example 11

Esterification of 5,20-acetonide, followed by deprotection of the obtained intermediate, to prepare ingenol 3-dodec-11-enoyl ingenol (example D of formula III structure, for Z=Z2).
Esterification 3.60 g of 5,20-ingenol acetonide (1.00 equiv; 9.27 mmol), produced according to example 7, were eluted in 80 mL of acetonitrile (22.2 volEquiv) with 4.13 g of 11-dodecenoic acid (1.50 equiv; 13.9 mmol, and 4.53 g of cesium carbonate (1.50 equiv; 13.9 mmol).

The reaction was monitored by HPLC analysis every 15 minutes at 214 and 290 nm in YMC Pro C18, 4.6×50 mm, 3 μm column, with A-B gradient of 5-70% in 7 minutes, at 1.5 mL/min. Solvents: solvent A—0.1% TFA in water, solvent B—0.08% TFA in acetonitrile.

The obtained intermediate, 5,20-isopropylidene-ingenol-3-dodec-11-enoyl, was then subjected to extraction and purification.

Extraction of the product of this step of the synthesis step in dichloromethane and water was performed. The organic phase was dried with magnesium sulfate and evaporated at 35° C./30'/10 Torr. This was followed by purification through solubilization in 5% ethyl acetate in heptane, and then applied in flash column containing 80 g of silica. The column was equilibrated with the same solvent. Thereafter, the column was washed with 5% ethyl acetate in heptane solution. The intermediate 5,20-isopropylidene-ingenol-3-dodec-11-enoyl was eluted in 10% ethyl acetate in heptane solution. Elution was monitored by HPLC with UV detector at 290 nm. The combined fractions were evaporated at 35° C./30'/10 mbar.
Deprotection For deprotection of the intermediate structure, 4.88 g of 5,20-isopropylidene-ingenol-3-dodec-11-enoyl (1.00 equiv, 8.29 mmol; 96%) were eluted in 80 mL of methanol (19.9 volEquiv) plus 4.60 mL of 1N hydrochloric acid (1M; 0.555 equiv; 4.60 mmol). This was followed by extraction with toluene and water. The organic phase was dried with magnesium sulfate and evaporated at 35° C./30'/10 Torr.

The person skilled in the art can readily evaluate, by means of the teachings contained in the text and in the presented examples, advantages of the invention, as well as propose modifications and equivalent alternatives to the embodiments not expressly presented herein, without departing from the scope of the invention, as defined in the attached claims.

The invention claimed is:

1. A pharmaceutical composition for the treatment of an HIV infection comprising one or more compounds of formula I

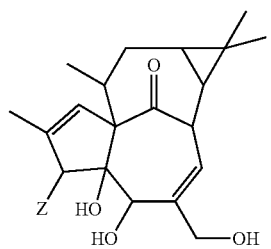

Formula I wherein Z is as follows:

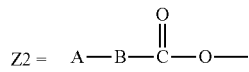

such that
A is phenyl, $CH_3$— or $CH_2$=CH—, and (B) is —CH=CH—, [—$CH_2$—]$_q$ or [—$CH_2$—]$_w$,
wherein q is an integer varying between 1 and 10, and w is an integer varying between 1 and 10, provided that:
when A is phenyl, B is —CH=CH—;
when A is $CH_3$—, B is [—$CH_2$—]$_q$;
when A is $CH_2$=CH—, B is [—$CH_2$—]$_w$; and
at least one anti-retroviral agent active against viruses under active replication.

2. The pharmaceutical composition according to claim 1, wherein said one or more compounds of formula I have the following structure:

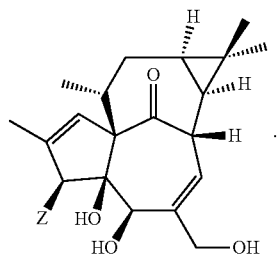

3. The pharmaceutical composition according to claim 1 wherein q varies between 2 and 6, and w varies between 8 and 10.

4. The pharmaceutical composition according to claim 1, wherein said compounds are one or more among A, B, C and D as follows:

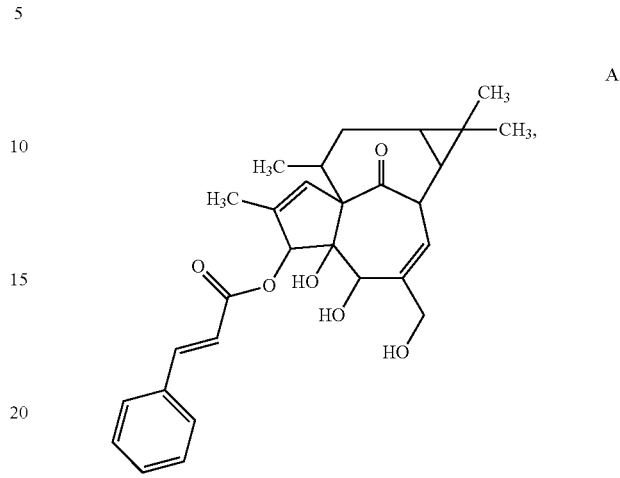

A

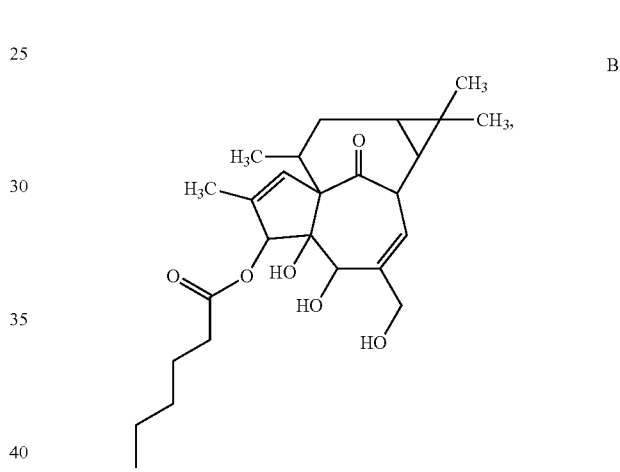

B

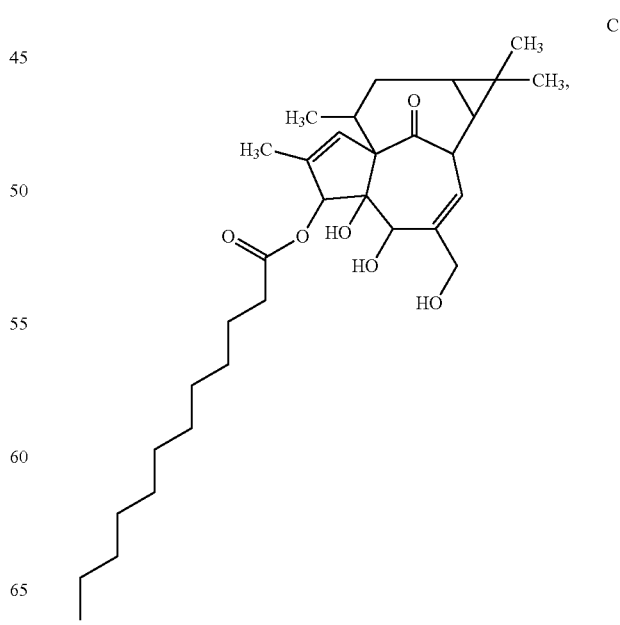

C

-continued

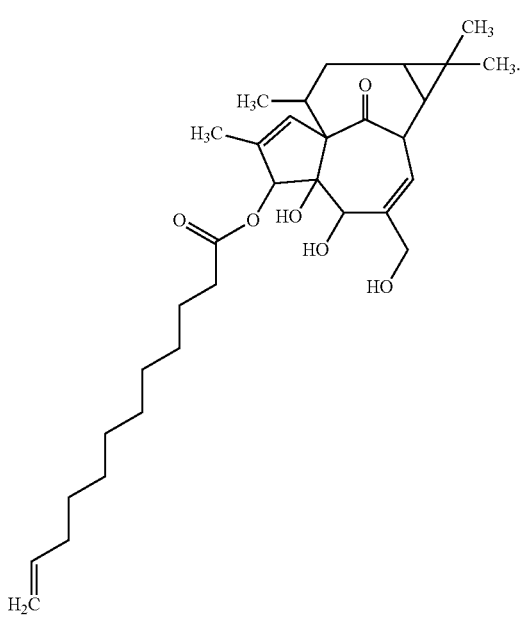

5. The pharmaceutical composition according to claim 1, wherein said at least one active anti-retroviral agent active against actively replicating viruses are selected from the group consisting of nucleoside or non-nucleoside reverse transcriptase inhibitors, protease inhibitors, co-receptor antagonists, retroviral integrase inhibitors, viral adsorption inhibitors, specific viral transcription inhibitors, cyclin-dependent kinase inhibitors and combinations thereof.

6. The pharmaceutical composition according to claim 1, wherein said one or more compounds of formula I and said one or more antiretroviral agents are comprised in the same dosage form.

7. The pharmaceutical composition according to claim 1 further comprising pharmaceutically acceptable excipients.

8. The pharmaceutical composition according to claim 1, further comprising one or more compounds configured to reactivate latent HIV virus other than the compounds of formula I, and also other than antiretroviral agents active against actively replicating viruses.

9. An adjuvant for treating infection caused by HIV virus, comprising one or more compounds of formula I according to claim 1 and pharmaceutically acceptable excipients.

10. Method of treating an HIV infection comprising administering to a patient in need of such treatment the composition of claim 1.

11. Method of treatment, according to claim 10, wherein the administration of components is concomitant or sequential.

12. A pharmaceutical composition for reactivation of latent HIV virus in viral reservoirs of a human body, comprising one or more compounds of formula I:

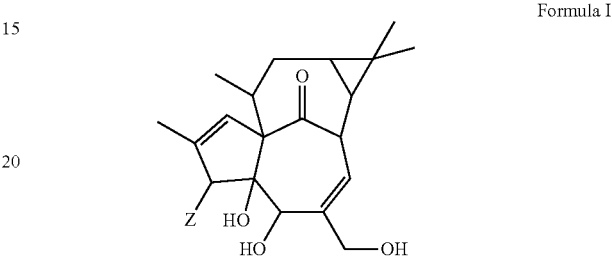

Formula I wherein Z is Z2 as follows:

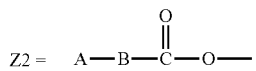

such that
A is phenyl, $CH_3-$ or $CH_2=CH-$, and B is $-CH=CH-$, $[-CH_2-]_q$ or $[-CH_2-]_w$,
wherein q is an integer varying between 1 and 10, and w is an integer varying between 1 and 10,
provided that:
when A is phenyl, B is $-CH=CH-$;
when A is $CH_3-$, B is $[-CH_2-]_q$;
when A is $CH_2=CH-$, B is $[-CH_2-]_w$; and
pharmaceutically acceptable excipients.

13. Method for reactivating latent HIV virus in viral reservoirs in the human body, comprising administering to a patient in need of such one or more composition of claim 12.

* * * * *